(12) United States Patent
Baroudi

(10) Patent No.: US 6,983,230 B2
(45) Date of Patent: Jan. 3, 2006

(54) METHOD AND APPARATUS FOR SIMULATING A RADIATION DOSE DELIVERED TO AN OBJECT

(75) Inventor: Bassam Baroudi, San Jose, CA (US)

(73) Assignee: Sterigenics US, Inc., Oakbrook, IL (US)

( * ) Notice: Subject to any disclaimer, the term of this patent is extended or adjusted under 35 U.S.C. 154(b) by 965 days.

(21) Appl. No.: 09/952,847

(22) Filed: Sep. 11, 2001

(65) Prior Publication Data

US 2003/0050769 A1    Mar. 13, 2003

(51) Int. Cl.
G06G 7/48    (2006.01)
G06F 19/00    (2006.01)

(52) U.S. Cl. ............... 703/6; 703/2; 700/29; 700/114; 434/218

(58) Field of Classification Search ............... 703/2, 703/6; 700/28, 29, 112, 114, 245; 434/218; 250/252.1, 580; 600/436; 378/143
See application file for complete search history.

(56) References Cited

U.S. PATENT DOCUMENTS

| | | | | |
|---|---|---|---|---|
| 4,331,021 A | | 5/1982 | Lopez et al. ............... 73/1.86 |
| 4,620,908 A | | 11/1986 | Van Duzer ............ 204/157.68 |
| 4,663,772 A | | 5/1987 | Mattson et al. ............ 378/18 |
| 4,976,266 A | * | 12/1990 | Huffman et al. ........... 600/436 |
| 5,375,158 A | * | 12/1994 | Logan ..................... 378/143 |
| 5,430,308 A | * | 7/1995 | Feichtner et al. .......... 250/580 |
| 6,157,028 A | | 12/2000 | Purtle ..................... 250/252.1 |
| 6,301,329 B1 | | 10/2001 | Surridge ................... 378/65 |

OTHER PUBLICATIONS

Petrosky et al. J.C. An Approach to Model Total Dose Ionizing Radiation Effects in Hg1-X CdXTe Photodiodes Using Pisces II-B+, IEEE Transactions on Nuclear Science, vol. 40, No. 6, Dec. 1993, pp. 1597-1601.*
Moore, C.J. Computerized Conformal Radiation Therapy—A Critical Process, IEEE Computing & Control Engineering Journal, vol. 6, No. 5, Oct. 1995, pp. 205-210.*
Frederickson, A.R. Concepts for Secondary Electron Emission from Irradiated Insulators, IEEE Int. Symposium on Discharges and Electrical Insulation in Vacuum, Jul. 1996, pp. 517-522.*

(Continued)

Primary Examiner—Russell Frejd
(74) Attorney, Agent, or Firm—Martine Penilla & Gencarella, LLP

(57) ABSTRACT

Methods and an apparatus for determining a radiation dosage received by a product being exposed to radiation in an irradiator cell through a computer simulation are provided. One exemplary method includes a computer simulation for determining radiation dosages received by a product to be passed along a radiation cell, where the product is to be stationary at a set number of locations within the cell is provided. The method initiates with a point on the product being defined. Then, pre-calculated lengths between the point on the product and the radiation source at each of the set of locations in the cell are identified. Next, a dosage of radiation to be received by the point on the product at each location is calculated using the pre-calculated lengths.

80 Claims, 9 Drawing Sheets

OTHER PUBLICATIONS

Barinov et al., N.U. Medical Equipment Sterilization Using Superhigh Dose Rate X-Ray Irradiation, IEEE 12th Int. Conference on High-Power Particle Beams, vol. 2, Jun. 1998, pp. 977-980.*

Zavadtsev, A.A. Equipment for Beam Current and Electron Energy Monitoring During Industry Irradiation, IEEE Particle Accelerator Conference, vol. 2, May 1997, pp. 2250-2252.*

Miller, R.B. Food Irradiation Technology Using Electron Beams and X-Rays, 3rd IEEE Int. Vacuum Electronics Conference, Apr. 2002, pp. 9-10.*

Stathakis et al., S. Dose Calculations with the BEAM Monte Carlo Code at Extended SSDs, Proceedings of the 22nd Annual EMBS International Conference, vol. 3, Jul. 2000, pp. 1679-1680.*

Dolgachev et al., G.I. Air Injected High Power Repetitive Electron Beam for Radiation Treatment, IEEE 12th International Conference on High-Power Particle Beams, vol. 2, Jun. 1998, pp. 981-984.*

G. Cohen et al., "Dosimetric Analysis of Ruthenium-106 Opthalmic Applicators for the Treatment of Retinoblastoma and Ocular Melanoma", Proceedings of the $22^{nd}$ Annual EMBS International Conference Jul. 23-28, 2000.

Milica Popovic et al, "Finite-Difference Time-Domain Analysis of a Complete Transverse Electromagnetic Cell Loaded with Liquid Biological Media in Culture Dishes", IEEE Transactions on Biomedical Engineering, vol. 45, No. 8, Aug. 1998.

* cited by examiner

METHOD AND APPARATUS FOR SIMULATING A RADIATION DOSE DELIVERED TO AN OBJECT

BACKGROUND OF THE INVENTION

1. Field of the Invention

This invention relates generally to methods and apparatus for predicting a radiation dose and more specifically to simulating the total radiation dose for a product undergoing irradiation at multiple points within an irradiation cell.

2. Description of the Related Art

Numerous manufactured goods, including medical devices and accessories, pharmaceutical or biotech manufacturing supplies, foods, etc., undergo exposure to radiation energy. This exposure is often required to reduce the counts of microorganisms and bacteria to acceptable levels or to alter the characteristics of the product or its materials. The exposure process, referred to as "sterilization" or "irradiation," is typically achieved by exposing the product to Gamma rays, X-rays or other radiation sources for a predetermined length of time to achieve the desired result. The result is expressed as a dosage, typically in units of Kilograys or Megarads, and is measured at one or more locations on and/or within the product volume. The longer a product is exposed to the radiation, the higher its dose.

For products requiring reduced microorganism count, the location of the minimum received dose is of special significance, since it is there that the highest residual microorganism count would likely remain after exposure. At the opposite extreme, exposure to too much radiation can adversely affect the characteristics of a product. For example, certain plastics turn yellow or craze when overexposed. Manufacturers are therefore interested in the locations and amounts of the minimum and maximum dose extremes in order to specify and verify processing parameters. Determination of these extremes is difficult, time consuming and imprecise. As described below, the determination of these quantities is highly dependent on a number of variables, many of which are unknown or uncontrollable at the time any given product is irradiated. The net result is that irradiated products may not receive the prescribed dosage during routine processing. The actual delivered dose can be verified using different methods, including radiation sensitive strips called "Dosimeters." This verification though can take place only during or after the radiation process. Accordingly, no guidance is provided for predicting or estimating doses that will be delivered to the product under any particular processing situation. Without any predictive capability, the product is at risk if the dosage delivered is outside of the minimum or maximum doses.

Since the materials used in the radioactive source, for example radioactive isotopes composed of Cobalt 60, can be expensive and dangerous to handle, the processing is done in specially built cells having thick concrete walls. The specialized knowledge, high capital costs and ongoing expenses involved in constructing, owning and operating such installations precludes most manufacturers from operating their own sterilization facilities. Instead, a number of firms provide contract sterilization services on the open market. The radioactive isotope is costly and constantly decaying (Cobalt 60 loses one-half of its potency every 5-¼ years), therefore, contract sterilization firms design their cells and schedule production runs to make efficient use of the radioactive source. Cells are typically designed to accommodate many different products simultaneously. In addition the cells are routinely arranged to fill as much of the cell volume as is practicable. Typically, a conveyor transports the product through a series of rows, arrayed on either side of the centrally located radioactive source material. The product moves through a series of predetermined positions, dwelling at each position for a predetermined period of time. In some cell configurations, products pass through the cell multiple times, each time at a different height or level.

The arrangement of products in numerous rows, sometimes on more than one level, means that a given product will clearly "see" the radioactive source only when it is in a row immediately adjacent to a source. Elsewhere, it will be partially shielded by products and other elements between it and the source. High density intervening product will absorb more of the incident energy than low density intervening product. The effect is severe enough so that under many conditions, the subject product will receive dosages outside the specified range. To avoid this unacceptable consequence, many products cannot be run with those that would adversely affect its dose. Faced with the need to fill the cell efficiently while remaining mindful of the dosage specifications of each product, cell operators employ certain heuristic rules when developing their daily production schedules. These rules typically rely on the product characteristics (for example, the product density) and characterization data taken on the subject product. The characterization data includes the collection of measured doses taken on a sample product under known conditions, in order to establish the parameters for future processing. Armed with the characterization data, product characteristics and the firm's scheduling rules, products are scheduled and selectively monitored to assure compliance.

Numerous problems result from this approach. Owing to the large number of products available to be processed at any given time, products are rarely run with the same product mix as when they were characterized. Since the surrounding product can have a substantial effect on the dose received by a given product as described above, some products are likely to exceed their processing specifications (i.e., fall outside the specified range). Moreover, since the minimum and maximum locations determined during characterization can shift when the product is processed under different conditions, a product could receive less than the specified minimum dose yet go undetected, thereby frustrating the essential purpose of sterilization. Additionally, the time and expense of placing dosimeters on products, and the logistics of handling, measuring and recording their values, makes it infeasible to exhaustively monitor every product in a production run. The diverse product mix, disparate processing specifications and delivery commitments must be reconciled into an efficient production schedule using only simple rules for inferring a resultant dose. The result is sub-optimal schedules that make poor use of the costly radioactive source, and the possibility of improperly delivered dosages. The present inability of the production scheduler to predict the effect of a production schedule on the dosages delivered to any product leads to reliance on subjective factors. Thus the achievement of consistent processing results becomes unattainable.

Public domain software such as QAD are not capable of being utilized in a production environment. These public domain methods employ classical ray tracing techniques but require individual, successive geometry definitions for every step in order to simulate the movement of a product past a radiation source. As the product advances through the predetermined positions, a new set of geometric definitions must be supplied at each position and exhaustively calculated, and the ray tracing techniques must be applied for each point at each predetermined position. The excessive amount of time required to run the ray tracing techniques, including the exhaustive geometric calculations performed at each step, and the burden of providing the input at each step as the product moves through the irradiator cell, renders the classical ray tracing techniques impractical for production use.

As a result, there is a need to solve the problems of the prior art to provide a method and apparatus for simulating the radiation dose for points on a product at each position of the product in the irradiator cell and a total radiation dose received for the points on the product through the irradiator cell.

SUMMARY OF THE INVENTION

Broadly speaking, the present invention fills these needs by providing a method and apparatus to simulate the radiation dosage received by a product at individual points within the irradiator cell and a total dosage of radiation received by the product while travelling within the cell. It should be appreciated that the present invention can be implemented in numerous ways, including as a process, an apparatus, a system, or a device. Several inventive embodiments of the present invention are described below.

In one embodiment, a computer simulation for determining radiation dosages received by a product to be passed along a radiation cell, where the product is to be stationary at a set number of locations within the cell is provided. The method initiates with a point on the product being defined. Then, pre-calculated lengths between the point on the product and the radiation source at each of the set of locations in the cell are identified. Next, a dosage of radiation to be received by the point on the product at each location is calculated using the pre-calculated lengths.

In another embodiment, a method for simulating a radiation dosage of a product traversing an irradiator cell having a radiation source from which rays of radiation emanate is provided. The method initiates with points on the product being identified. Then, source points on the radiation source are identified. Next, zones within the irradiator cell are defined where each zone is defined along a path. Then, effects of the zones on the rays of radiation travelling from the source points to the product is calculated. Next, the effects for each of the points on the product is accumulated to provide a radiation dosage received by each of the points on the product.

In yet another embodiment, a computer simulation method for predicting a radiation dosage received by dosimeters on a product where the product is exposed to radiation from a radiation source in an irradiator cell while stopping at a set of positions within the cell is provided. The computer initiates by defining a location for each of the dosimeters within the irradiator cell at each of the set of positions. Then lengths from a set of source points on the radiation source to each of the dosimeters at each of the set of positions is calculated. Next, the defined locations and the calculated lengths are stored in a data structure. Then, the radiation dosage received by each of the dosimeters at each of the set of positions is determined using the calculated lengths.

In still another embodiment, a method for simulating a radiation dosage to be received by a product in an irradiator compartment is provided. The method initiates with a geometry of the irradiator compartment being read. Here, zones are established, constant zone lengths for each zone are calculated and the constant zone lengths are stored. Then, a receiver point array defined. The receiver point array includes a set of entries for a dosimeter at a plurality of positions of the product as the product is advanced through the compartment. Next, rays are calculated and traced through each of the zones. Here, the rays are defined between each of a plurality of source points to the dosimeter of the product as the product is advanced through the compartment. Each ray defines ray segments, where the ray segments have lengths defined by the constant zone lengths. Then, partial dosages for each of the traced rays are calculated. Next, the partial dosages are accumulated to provide a total dosage for the dosimeter once the product has completed its path through the compartment. Then, the total dosage for the dosimeter of the product is presented.

In still yet another embodiment, a method for simulating dosage levels for a product receiving radiation emanating from a treating source is provided. The method initiates with establishing source points where the source points are located on the treating source. Then, ray lengths for each of the source points are calculated. Here, each of the ray lengths represent a path from the source points to a dosimeter associated with the product. Next, zone lengths for each of the ray lengths are identified. Then, zone materials are identified. Next, an effect on the dosage level received by the dosimeter from the treating source by each zone material for each zone length is computed. Then, a sum of partial dosages received by the dosimeter from each of the source points is accumulated.

In another embodiment, a method for predicting a dosage level received by a product as the product is processed through successive stop locations in an irradiator cell, where the irradiator cell includes a radiation source and the radiation source is defined by source points is provided. The method initiates with the geometry of the irradiator cell being read, where the geometry characterizes zones of the irradiator cell as fixed zones and variable zones. Then, a zone characteristics array and a dosimeter data array are initialized. The zone characteristics array includes material compositions for the fixed zones and a default material composition for the variable zones. The dosimeter data array includes coordinates for each dosimeter associated with the product. Next, a production schedule is read. The production schedule contains names of each dosimeter for the product, a product dwell time for each stop location and variable material compositions for the variable zones, where the variable material compositions are substituted for the default material compositions. Then, receiver point arrays are created where each receiver point array corresponds to each dosimeter of the dosimeter array. Each receiver point array includes an entry for each stop location of the product, where each entry includes dosimeter absolute coordinates. Next, source point arrays are created where each source point array corresponds to each entry of each of the receiver point arrays. Each source point array includes fixed zone effects, the fixed zone effects reflecting a fixed zone attenuation. Then, a tracing of rays between each source point and each dosimeter is calculated. Next, a zone length array is accessed, the zone length array includes a ray length for each ray through each zone. Then, the variable material compositions for the variable zones are obtained. Next, an attenuation of the radiation source for each of the variable zones of each ray length for each source point is computed where each ray length is retrieved from the zone length array. Then, the dosage level through each zone for each ray at each stop location for the dosimeter is accumulated. Next, the accumulated dosage levels from each stop are summed to provide a total dosage for each dosimeter through the irradiator cell.

In another embodiment, a method for predicting an amount of radiation to be received by a product in a treatment compartment is provided. The method initiates with defining a material type for the product. Then, placements of the product within the treatment compartment are defined. Next lengths between a radiation source and the product for each of the placements within the treatment compartment are pre-calculated. Then, a final predicted radiation dose, using the pre-calculated lengths, to be received by the product if subjected to treatment at each of the placements within the treatment compartment is calculated.

In yet another embodiment, a method for modeling a dosage level for a product to be exposed to a radiation source in an irradiator cell is provided. The method initiates with data files being read, where the data files define cell geometry, material compositions and dosimetry specifications. Then fixed zones and variable zones are defined. Next, rays are traced between source points of the radiation source and dosimeters of the product. Then, zone lengths of the rays through each fixed and variable zone which the traced rays pass are ascertained. Next, fixed zone materials and variable zone materials are identified. Then, a fixed zone attenuation and a variable zone attenuation of the radiation source is computed. Here, the fixed zone attenuation and the variable zone attenuation are accumulated for each dosimeter location as the product advances through the irradiator cell. Next, the accumulated fixed zone attenuation and the variable zone attenuation are summed to predict a dosage level for each dosimeter.

In another embodiment, a method for determining dosages received by a product to be exposed to a treatment source at at least one defined location from the treatment source is provided. The method initiates with defining a point on the product. Next, fixed zones and variable zones are defined. Then, pre-calculated lengths between the point on the product and the treatment source at each of the at least one defined location are identified. Next, a dosage of treatment received by the point on the product at each of the at least one defined location is calculated using the pre-calculated lengths.

In still another embodiment, a computer readable medium having program instructions for simulating radiation dosages received by a product to be passed along a radiation source in a cell and where the product is to be stationary at a set number of locations within the cell is provided. The computer readable medium includes program instruction for defining a point on the product. Program instructions for identifying pre-calculated lengths between the point on the product and the radiation source at each of the set of locations in the cell are included. Program instructions for calculating a dosage of radiation to be received by the point on the product at each location using the pre-calculated lengths.

In still yet another embodiment, an apparatus for irradiating a product is provided. The apparatus includes a cell configured to contain radiation. A radiation source located within the cell and a transport mechanism are also included. A product being transported using the transport mechanism through the cell is included. The product is associated with at least one dosimeter where the product and dosimeter receive a radiation dosage from the radiation source. The radiation dosage is capable of being defined by a simulation prior to the product entering the cell, wherein the simulation identifies pre-calculated lengths between the dosimeter and the radiation source and uses the pre-calculated lengths to determine the radiation dosage received by the dosimeter.

In another embodiment, an apparatus for exposing a product to a treatment is provided. The apparatus includes a treatment cell configured to enclose a product path. A treatment source within the treatment cell is included. A product being exposed to the treatment from the treatment source while travelling along the product path is included, where the treatment exposure of points on the product is predicted by a computer simulation prior to the product entering the treatment cell. The computer simulation is configured to obtain lengths of treatment rays from the treatment source to the points on the product based upon a geometry of the treatment cell, where the lengths of the treatment rays are used to calculate a dosage of treatment received by the points on the product while travelling along the product path.

In yet another embodiment, a treatment system is provided. The treatment system includes a general purpose computer for controlling robotics associated with a treatment compartment of the treatment system. The general purpose computer further includes code for predicting treatment dosages to be received by a product from a treatment source located within the compartment where the code for predicting uses pre-calculated product positioning parameters.

The advantages of the present invention are numerous. Most notably, the storage of the zone lengths for repeated use in calculating the dosage received by a product in a cell allows for predicting a radiation dosage received by the product, which is not feasible without the method and apparatus. In addition, the simulation can be applied to any irradiation cell irrespective of the configuration of the cell.

Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings, and like reference numerals designate like structural elements.

DETAILED DESCRIPTION OF THE PREFERRED EMBODIMENTS

Figure 1:
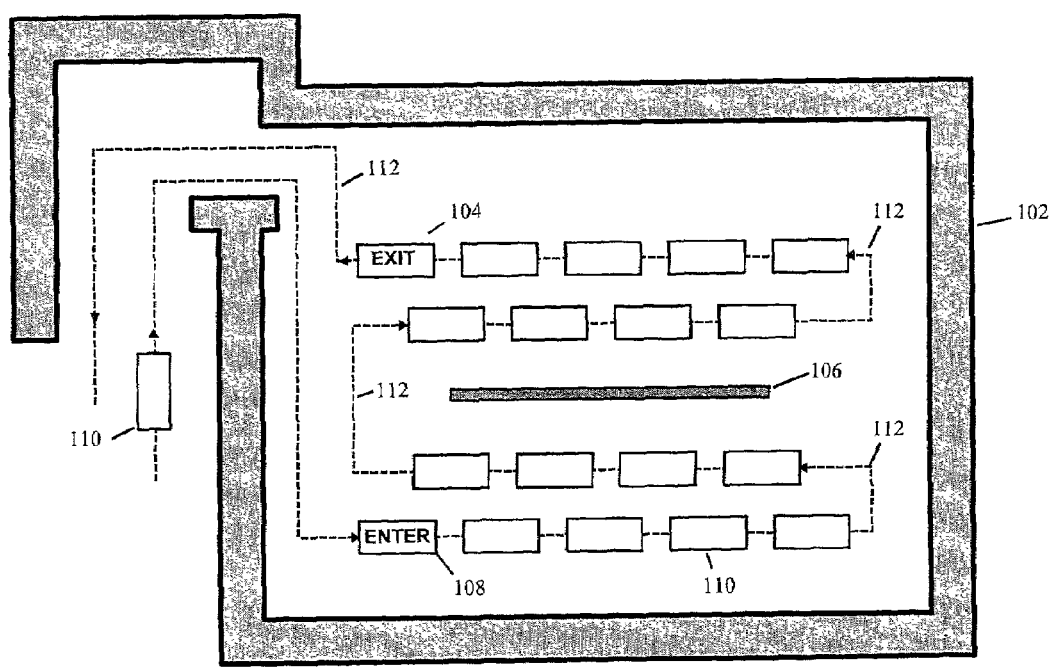
FIG. 1 illustrates a block diagram displaying a plan view of an irradiator cell in accordance with one embodiment of the invention.

An invention is described for an apparatus and method for simulating the radiation dosage of a product in an irradiator cell as the product proceeds through the cell. It will be obvious, however, to one skilled in the art, that the present invention may be practiced without some or all of these specific details. In other instances, well known process operations have not been described in detail in order not to unnecessarily obscure the present invention.

The embodiments of the present invention provides a means to quickly simulate the process and to predict the dose expected in any given production schedule to a known certainty. By monitoring and reporting an arbitrarily large number of locations well in advance of the physical processing, the present invention enables a scheduler to effectively preempt dosing errors for every carton in every product run in a production schedule. In one embodiment, the geometry of the irradiator cell, the composition of the products being irradiated and the dosimetry specifications are provided in data structures. Of course, the cell can be a compartment designed to safely contain the radiation from the radiation source and to allow for the transportation of the product into and out of the compartment Through the geometry of the cell and the coordinates of the dosimeters, rays are traced from source points of the radiation source to the dosimeters on the product in one embodiment. Each of the rays pass through various zones, and these zone lengths are pre-calculated and stored in another embodiment. For example, totes containing various products may be in the path of the ray trace. Accordingly, the wall of the totes, the product within the totes and the air between the source and the totes all define different zones. It should be appreciated that the size of a product tote could be made variable by subdividing it into multiple zones. In one embodiment, a partial dosage for each dosimeter is calculated and accumulated at each location of the product as it progresses through the irradiator cell. The incremental dose accumulations are then summed and presented, thereby allowing for a timely and accurate approximation of the dosage received at each dosimeter of the product.

In one embodiment, the present invention takes advantage of the repeatability of the stop locations, dosimeter locations and arrangement of the product-tote materials. For example, the dosimeter-source point ray lengths along geometric quantities, known as zone lengths, are pre-calculated and saved in one embodiment. To facilitate the pre-calculations, variable and fixed zones are identified based upon the cell geometry. For example, each traced ray may enter and exit numerous "zones," each containing a different material. Certain zones, for example those containing the source racks or mechanics of the transport system within the cell (e.g., stainless steel), will always contain the same materials, i.e., fixed zone material. Zones represented by a product tote or totes will change from step to step depending on the contents of the product tote as defined in a production schedule. The composition of this zone material is not known until the product is read from the input, hence it is referred to as variable zone material. The composition of all zone materials has an impact on the dose calculation and thus must be accounted for when performing the dose calculations. During ascertainment of the zone lengths, both fixed and variable zone materials are identified in one embodiment. The effects of fixed zone material is pre-calculated and saved along with markers representing the variable-zones and the zone lengths in another embodiment.

During the simulation process, the actual product tote material is substituted for the variable zone markers as the information is read from the input. Thus, the pre-calculated zone lengths and fixed zone materials are used repeatedly without computational penalty. Additionally, the previously identified variable zone markers facilitate "on-the-fly" substitution of the marker with the actual material in the variable zones as the input is read, thereby further avoiding computational penalty. The method used by the present invention thus reduces the computational cost of calculating the geometric quantities to the extent that several days of production for a cell many times more complex than the example cell shown in the illustration of FIG. 2 can be accomplished in minutes.

Figure 2:
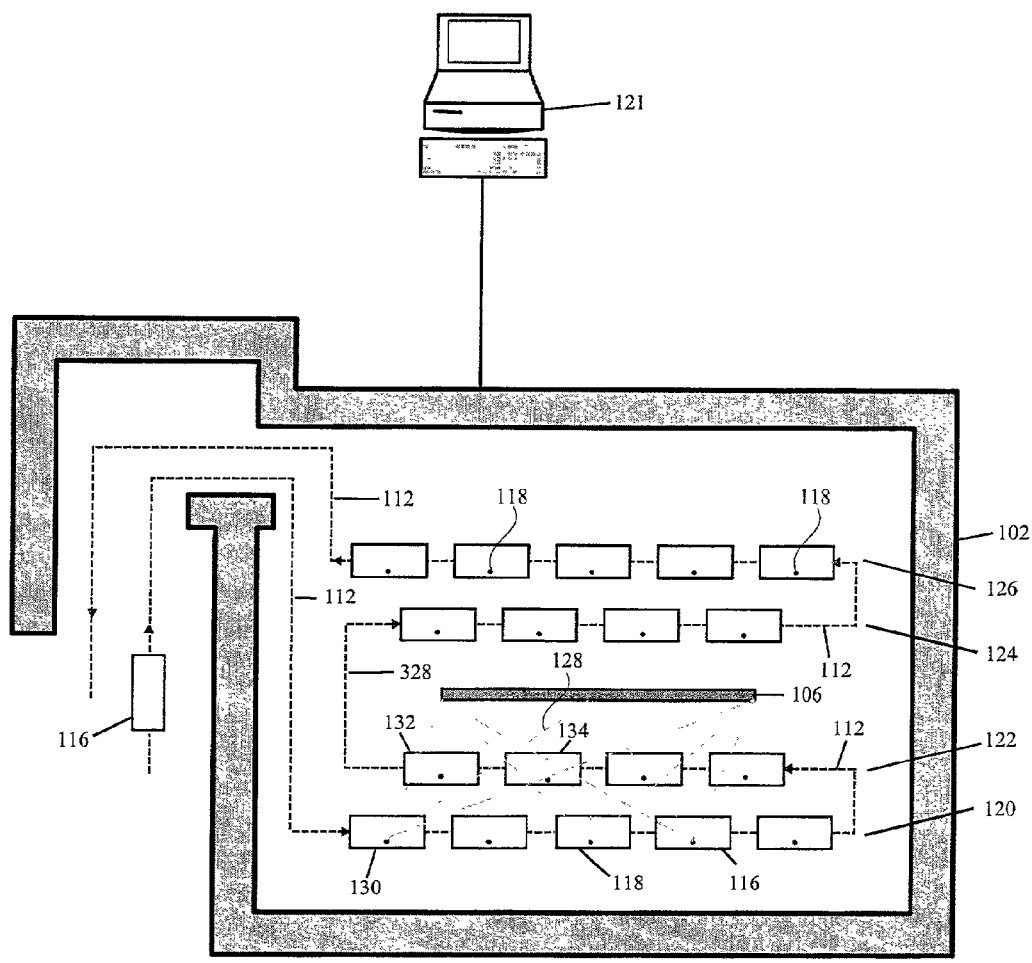
FIG. 2 illustrates a block diagram displaying a plan view of an irradiator cell having stop locations along a path in which zone lengths are represented in accordance with one embodiment of the invention.

FIG. 1 illustrates block diagram 100 displaying a plan view of an irradiator cell in accordance with one embodiment of the invention. In the irradiator cell of FIG. 1, product tote 110 enters cell 102 having radioactive source 106, and stops first at enter position 108, where it dwells for a predetermined period of time. Product tote 108 then proceeds through successive stop locations along path 112, dwelling for predetermined (but not necessarily equal) periods of time before moving on to the next stop location. At the same time that a tote moves from the enter position 108 to the next location, another tote enters the cell 102 and dwells at the enter location 108. After product tote 110 has dwelled at exit position 104 completing the exposure cycle, product tote 110 exits the cell 102. This process is repeated until all the product totes that entered the cell have exited the cell. In the descriptions that follow, the enter and exit positions conceptually relate to those illustrated in FIG. 1. In all cell configurations, the concept of a fill or enter position indicates the first place of dwelling in the cell 102, and a stop or exit position indicates a final place of dwelling in the cell 102. Other embodiments of the irradiator cell 102 includes more than one vertically separated "shelves", more than one pass through the cell or tote rotation. As will be demonstrated below, any configuration or geometry of the cell 102 can be accommodated with the embodiments of the invention FIG. 2 illustrates block diagram 114 displaying a plan view of an irradiator cell 102 having 18 stop locations along a path 112 in which zone lengths are represented in accordance with one embodiment of the invention. Product tote 116 enters and begins its path through the cell on row 120, moving from left to right. At the end of row 120, product tote 116 slides to row 122, where it moves from right to left past source 106, stopping at each location in row 122. At the left side of row 122, product tote 116 slides to row 124, where it moves rightward past source 106, one stop at a time. Upon reaching the end of row 124, product tote 116 slides to row 126, where it moves leftward one stop at a time until it exits the cell. It should be appreciated that the movements could be any arbitrary combination of slides and/or rotations, depending on the design and configuration of the irradiator cell. Additionally, the rows can be at different heights within the cell. The movement described above through cell 102 is for illustrative purposes and not meant to be limiting.

Continuing with FIG. 2, a dosimeter 118 is inside product tote 116. It should be appreciated that in the prior art a physical dosimeter would be affixed to product tote 116 at location 118. Additionally, other physical dosimeters would also be affixed to the product tote in the same or other locations, as determined by the product characterization steps. The dosimeters would then be read by calibrated equipment at the conclusion of the product run to determine the amount of dose delivered to product tote 116. In one embodiment of the present invention, dosimeters can be simulated at any number of points in all product totes. Furthermore, the simulated movement mimics the physical movement of the product totes through the cell. Here, dosimeter 118 refers to the simulated dosimeter placed by the present invention. In other words, the dosimeter refers to a point with respect to the present invention.

In one embodiment of the invention, the precise location of dosimeter 118 and others that may be affixed to a product tote such as product tote 116 are specified with respect to a reference location within the product tote 116. It is therefore possible to affix dosimeters to the same locations within a product tote with reproducible accuracy. Similarly, irradiation cells such as cell 102 are configured and built so that the product tote 116 stop at precisely the same locations each and every time the product totes traverse the cell. Therefore, any given dosimeter location within a product tote will always return to the same absolute cell location whenever traversing the same route through a cell. Just as important, the size of the product tote remains constant, so the dosimeter will also "see" the same number of surrounding bodies and orientations at each stop location as on previous and future traversals through a cell, even though the contents of the product totes may be different.

Referring back to FIG. 2, the dosimeter 118, regardless of which tote it is affixed to, will always return to the same precise 18 stop locations within cell 102 whenever product tote 116 traverses the cell along path 112, and will be surrounded by the same geometric environment at each stop. In one embodiment of the invention, in order to simulate dosages to a useful level of accuracy, the radioactive source is approximated by dividing it into many source points. A simplified example of the nature of the geometric calculations is illustrated in FIG. 2. For illustration purposes, only 3 product totes 116, and 3 zone rays 128 are shown per tote. In actuality, several hundred per dosimeter 118 (and others as may be assigned) per product tote are possible. As can be seen, the path traversed by each ray between a dosimeter and its respective source points passes through many different materials. Thus, each ray is unique and must be calculated accurately and separately from all others.

Dosimeter 118 of block diagram 114 is situated within product tote 116, which moves from left to right in row 120 along path 112. At each stop location, a separate ray must be traced between each of numerous separate source points within source 106 and dosimeter 118. For example, the middle ray 128, arriving at dosimeter 118, originates in the source material embedded in source 106. The ray next passes through the support material in source 106. The ray then travels through air, then the product tote in row 122 at location 134, then air, then the product tote in row 122 at location 132, then again through air and finally, through the product tote 116 in row 120 at location 130 before terminating at dosimeter 118. In one embodiment, the zone lengths for each of the rays through each of the zones is pre-calculated and stored as described in more detail in reference to FIG. 6. It should be appreciated that product totes in row 120 and 122 which the ray passes through are considered variable zones while the support material and the air are considered fixed zones.

Figure 3:
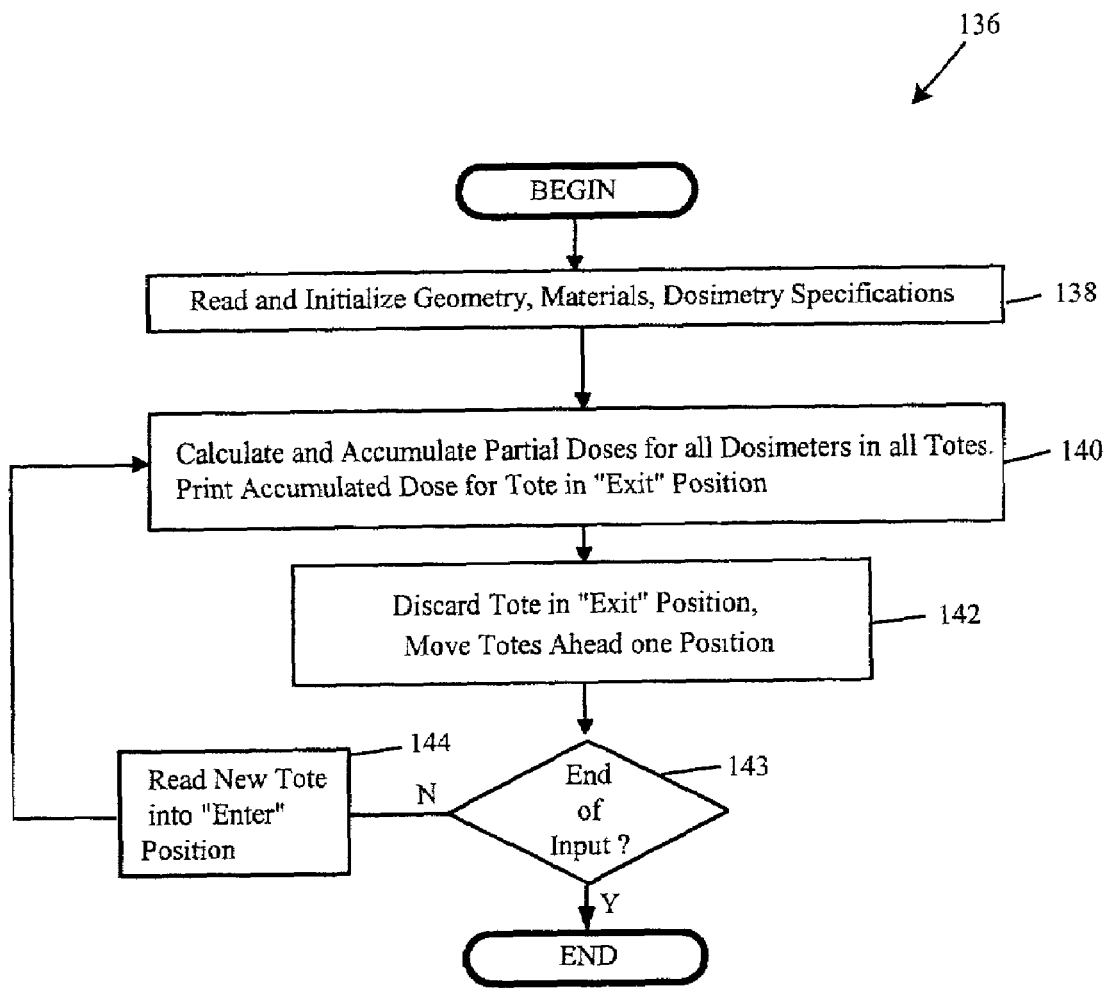
FIG. 3 displays a flowchart depicting an overview of the overall method in accordance with one embodiment of the invention.

FIG. 3 displays flowchart 136 depicting an overview of the overall method in accordance with one embodiment of the invention. The method initiates with operation 138, where data files describing the cell geometry, material compositions for the fixed-zone materials (e.g., totes, carriers, source rack), default materials for the variable-zone materials (i.e., the products to be irradiated) and the coordinates and name tags for each dosimeter are read. Here, the method acquires information corresponding to the cell and product geometry data. The process analyzes the geometry to determine whether a shape corresponds to a fixed zone (i.e., part of the cell structure) or to a variable zone (i.e., product tote contents). In one embodiment of the invention, the material inside the area defined by the fixed zone is the same for every cycle or stop location, while the material inside a variable zone can change from cycle to cycle or stop location to stop location. In addition, the material composition data corresponding to fixed zones is acquired to initialize a zone characteristics array. In one embodiment, default material composition data for variable zones are also used to initialize the zone characteristics array. The variable zone entries will be overwritten during execution, "on-the-fly," with actual product material composition, as the production schedule is read from the input. The material composition data are used during computation of the dosages as will be explained in more detail in reference to FIGS. 4 and 7.

Specifications for dosimeters, including their tag names and coordinate locations relative to the origin of the product tote, are read and used to initialize a dosimeter data array. These dosimeters then become known to the process and are used to determine the validity of dosimeters read from the input file. In one embodiment, naming conventions are used to identify the location of the dosimeters. Here, the totes may be divided into geometric quantities or according to a grid scale. It should be appreciated that any point on the grid scale or geometric quantity may be defined relative to the product tote. The product tote-relative coordinates are also used during the zone length process step, described in more detail in reference to FIG. 6, to compute the absolute location of each dosimeter in each product tote location throughout the cell. As is well known in the art, methods of storing and retrieving initialization data such as those described here can be accomplished via a computer disk medium, a local computer network, the Internet, etc. Similarly, methods of organizing and formatting such data within an input file or data stream are also well known in the art. By way of example, any of the data files described here, including the production schedule read as input, could be generated manually using an ordinary text editor, a spreadsheet program, generated automatically from a data base, etc.

Once initialization is complete, the method moves to operation 140 where the partial dosages are calculated for all dosimeters in every tote and summed to their respective accumulators. The dose, having fully accumulated in the product tote in the exit position, is then presented. Next, the method advances to operation 142 where the product tote at the exit position is discarded, every tote is stepped ahead by one position, and a new product tote is read from the input into the enter position. Then, the method proceeds to operation 143 where it is verified whether all the totes have been processed through the cell, i.e., whether there is additional input. If all the totes have not been processed, the method advances to operation 144 where a new tote is read into the enter position and operations 140, 142 and 143 are repeated until all the totes have been processed. If all the totes have been processed i.e., the input is exhausted, the process terminates. In another embodiment, the process could remain active and monitor an input stream where it would continue processing as new input is received.

Figure 4:
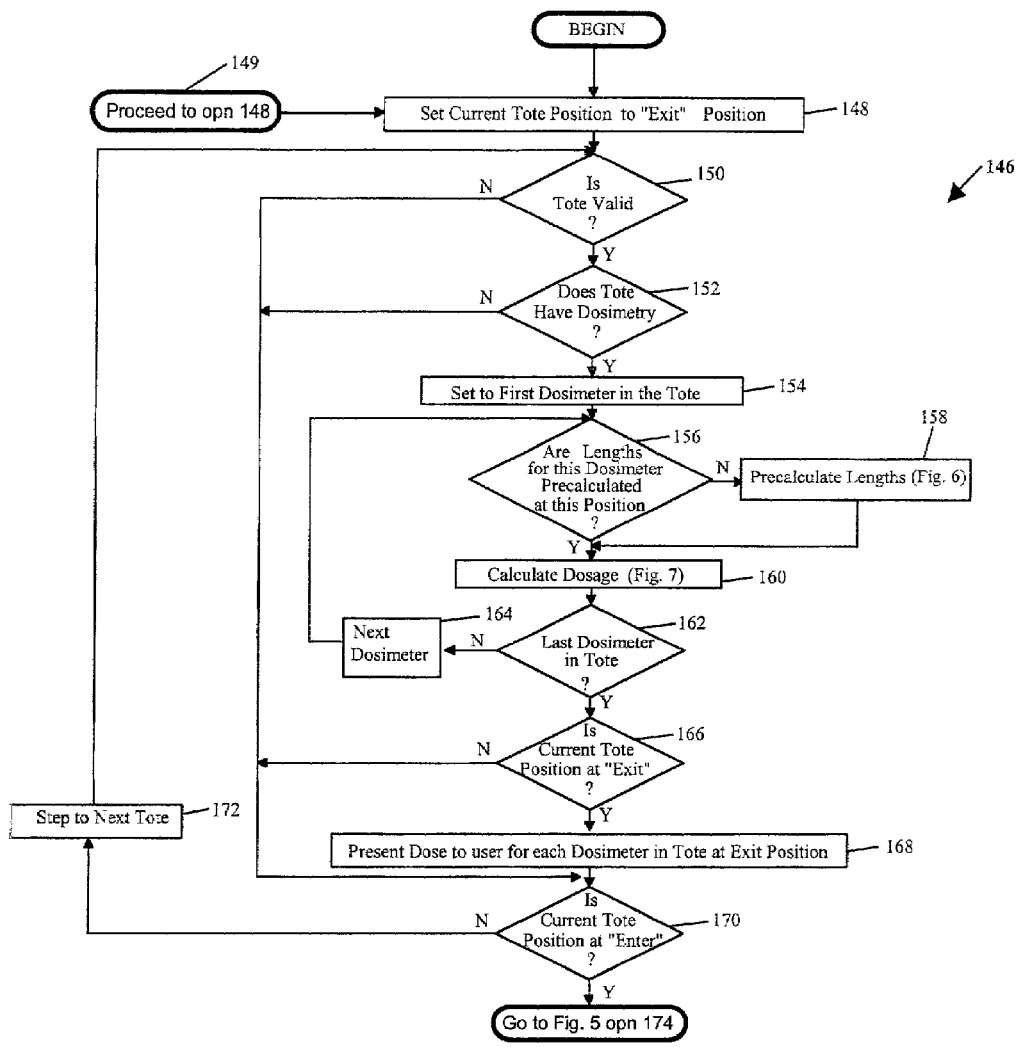
FIG. 4 displays a flowchart which is a more detailed description of the operation where the partial dosages are calculated for all dosimeters in every tote and summed to their respective accumulators in accordance with one embodiment of the invention.
Figure 5:
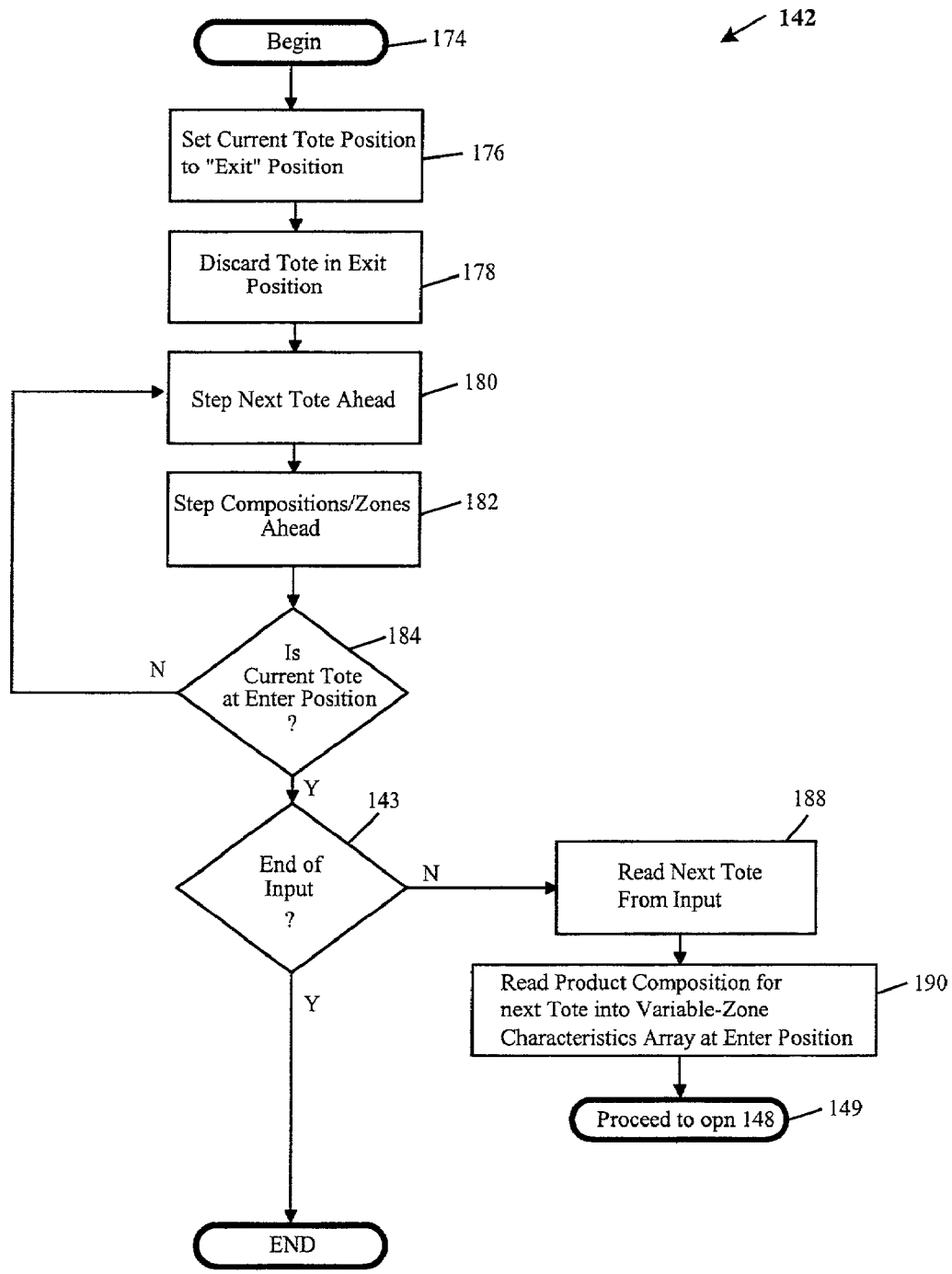
FIG. 5 displays a flowchart a more detailed description of the operation where product totes are advanced through the cell via the Free/Step/Fill Loop.

FIG. 4 displays flowchart 146 which is a more detailed description of operation 140 where the partial dosages are calculated for all dosimeters in every tote and summed to their respective accumulators in accordance with one embodiment of the invention. The method initiates with operation 148 where the current tote position is set to the exit position, which allows for the product tote presently in the exit position to be analyzed. Input from operation 149 of FIG. 5 is provided to operation 148. The input from operation 149 will be described in more detail with respect to FIG. 5. The method advances to operation 150, where it is determined whether the product tote in the exit position of operation 148 is valid. In the embodiment of the initial loading of the cell, no product data have yet been read from the input, i.e., this product has only default material and thus is not a valid production tote. In other words, for the initial loading of the cell the only valid tote is the tote just moved into the enter position 108 of FIG. 1. It should be appreciated that an empty tote can be a valid tote in one embodiment of the invention. Had the tote material been valid, the process would have continued to operation 152 where it would determine whether dosimeters had been specified. However, having determined that the present tote is not valid, the process moves from operation 150 to operation 170, where it tests whether the current tote position is at the enter location. In the embodiment where the irradiation process has just started, the current tote position is still pointing to the exit location, thus, operation 170 directs the method to operation 172, where the next tote position is selected. The process then returns to operation 150 and continues through operation 170 as before until a complete pass is made of all product totes in the cell. Upon reaching the enter position, operation 170 directs the process to operation 143 of FIG. 5.

FIG. 5 displays flowchart 142, showing a more detailed description of operation 142 where product totes are advanced through the cell via the Free/Step/Fill Loop. In operation 176 of flowchart 142, the current tote position is set to the exit position. Next the method proceeds to operation 178, where the product tote is discarded, making room for the remaining totes to be advanced. It should be appreciated that upon initial loading of the cell, the product tote at the exit position is a dummy tote i.e., not valid, for purposes of initializing the method in one embodiment of the invention. Then, in operation 180 the next tote is advanced ahead one position. Here, the tote in the position prior to the exit position is advanced to the exit position and each preceding tote is moved ahead one position. The current tote position is then set to the position prior to the exit position. In one embodiment, the dosimetry specifications contained in a data structure are advanced along with the tote. In another embodiment, the variable zone materials are advanced to correspond to the tote positions advanced in operation 180. The method then proceeds to operation 182 where the compositions and zones for the tote advanced in operation 180 are moved ahead. As is well known in the art, methods for advancing array data, such as the tote and variable zone data described here and in reference to FIG. 8, can be accomplished by moving the data itself among the arrays, by modifying the indexes pointing to array data, by modifying pointers to the data, by moving pointers to the data, by combinations of these techniques, etc. In a preferred embodiment, the indexes are modified to advance the array data. The method then moves to decision operation 184, where it is determined whether the current tote position is the enter position. Where the process has just started, it should be appreciated that the current tote position has moved from the exit position to the position prior to the exit position, thus operation 184 directs the method to operation 180, where the current tote position is advanced to the next tote. In one embodiment, this loop continues until the current tote position reaches the enter position.

Once the current tote position reaches the enter position, the method of FIG. 5 proceeds to decision operation 143, where it is determined if all the input has been entered. If all the totes have been processed i.e., the input is exhausted, the process terminates. If all the totes have not been processed, then the method advances to operation 188 where the production schedule is read from the input. In one embodiment, the production schedule contains data describing the name of the product, its effective density or optionally, its weight and the dimensions of the product. In another embodiment, the latter optional information is used in a special step to enhance the accuracy of the dose calculations. A product's effective density is the density a product would have if its smaller, denser volume were homogenized over the larger tote volume. To enhance the accuracy obtained from the effective density alone, the optional weight and dimensions are used in the dose calculations to account for the actual product dimensions. In yet another embodiment, the production schedule contains the names of dosimeters that are to be placed in the product tote, signifying where in the product tote doses are to be calculated and the length of time this product tote dwells at each stop location in the irradiator cell. It should be appreciated that the data structure for the tote i.e., dosimeter locations from the dosimeter array, is read in operation 188.

Continuing with FIG. 5, the method then advances to operation 190, where the material composition for the product tote at the enter position is read and inserted into the variable zone characteristics array at the location corresponding to the enter position. The dosimeters are added to the dosimeter array, where they will be used in a later step to compute zone lengths. In one embodiment, the composition data structure provides the composition and the attenuation of the material in the variable zone. It should be appreciated that operations 188 and 190 are a more detailed description of operation 144 of FIG. 3 where a new tote is read into the enter position. The method then advances to operation 149, thereby returning to operation 148 of FIG. 4, where the process of determining the validity of a product tote, described above, repeats via operations 150 through 172 until the next valid product tote is detected at operation 150.

Returning back to FIG. 4, operation 149 directs the method to operation 148 where the current tote position is set to the exit position. It should be appreciated that a valid tote has been introduced into the enter position after completion of the free/fill/step loop of FIG. 5 and that product totes read during prior iterations through the free/fill/step loop of FIG. 5 exist between the enter and exit positions. Accordingly, the method proceeds through operations 150, 170 and 172 until it reaches the next position containing a valid tote. Once at the next valid tote position, operation 150 determines that the product tote in the current tote position is valid and the method proceeds to step 152.

Continuing with FIG. 4, operation 152 determines whether dosimeters are present in the product tote. If the product tote contains no dosimeters, the method would branch to operation 170, bypassing the dose calculations. If the product tote contains dosimeters, the method proceeds to operation 154 where the first dosimeter in the tote is selected. Here the method will proceed to calculate the dose for each dosimeter situated within the product tote as described below. The method then advances to decision operation 156 where it examines the corresponding entry in the dosimeter array. If the method determines that the zone lengths for the current dosimeter have not been computed, it proceeds to operation 158 and computes the zone lengths for the current dosimeter for each of potentially hundreds of source points. As described above, the source points represent areas on the radiation source. For example, in one embodiment cobalt pencils are used as the radiation source. The cobalt pencils may be aligned in a row that contains 75 cobalt pencils. Each pencil may be divided into four source points which correlates to 300 total source points. Of course, there may be more or less source points and pencils depending on the configuration of the irradiator cell. The process for computing the zone lengths of operation 158 will be described in greater detail with respect to FIG. 6. Having completed the zone length calculations, the method advances to operation 160, where the dosage for the current dosimeter is calculated, then summed to the accumulator for the current dosimeter. The process for calculating the dosages for operation 160 will be described in greater detail later in FIG. 7.

The method of flowchart 146 then proceeds to decision operation 162, where it is determined whether the current dosimeter is the last dosimeter in the product tote to be calculated. If another dosimeter remains, the method proceeds to operation 164 where the next dosimeter is located. If there are more dosimeters in the tote, then the zone lengths are pre-calculated and/or dosages for the dosimeter at that stop location are calculated as described above. In one embodiment, the dosimeter data array contains the tote relative coordinates for each dosimeter within each product tote, as will be discussed in more detail in reference to FIG. 8. If the current dosimeter is the last one in the product tote, the method moves to operation 166 where the method determines whether the current tote position is at the exit position. If the current tote position is not at the exit position, the method branches to operation 150 where it continues the Calculate/Print Loop as described above beginning with operation 150.

When all rays from all source points to all locations that a dosimeter will occupy in each and every product tote location between and including the exit and enter positions are calculated, the dosimeter is marked as calculated. It should be appreciated that this process takes multiple iterations through FIGS. 4 and 5. If operation 166 determines that the current tote position is the exit position, the method proceeds to operation 168, where the total amount of dose delivered to each dosimeter location for the product tote in the current tote position is presented. The format and method of presenting this data can be accomplished in numerous ways. By way of example, the results could be sent to a computer disk file, over a local computer network, over the Internet, directly to a display screen, etc. In one embodiment, the results are printed to a standard output pipe, which is typically directed to a computer disk file. Once all the dosimeter locations have been printed, the method proceeds to operation 170 where the current tote position is tested to determine whether it is at the enter position. The method then proceeds through the remaining totes, as described above with respect to FIGS. 4 and 5, until the end of the input file is reached and detected in FIG. 5, operation 143. Upon determining that the input is exhausted in operation 143, the method stops processing and exits. It should be appreciated that in another embodiment, the method would not stop processing and exit but would wait for further input, then continue processing as input is received, thereby enabling the prediction of dosages concurrently with the actual physical treatment process.

Figure 6:
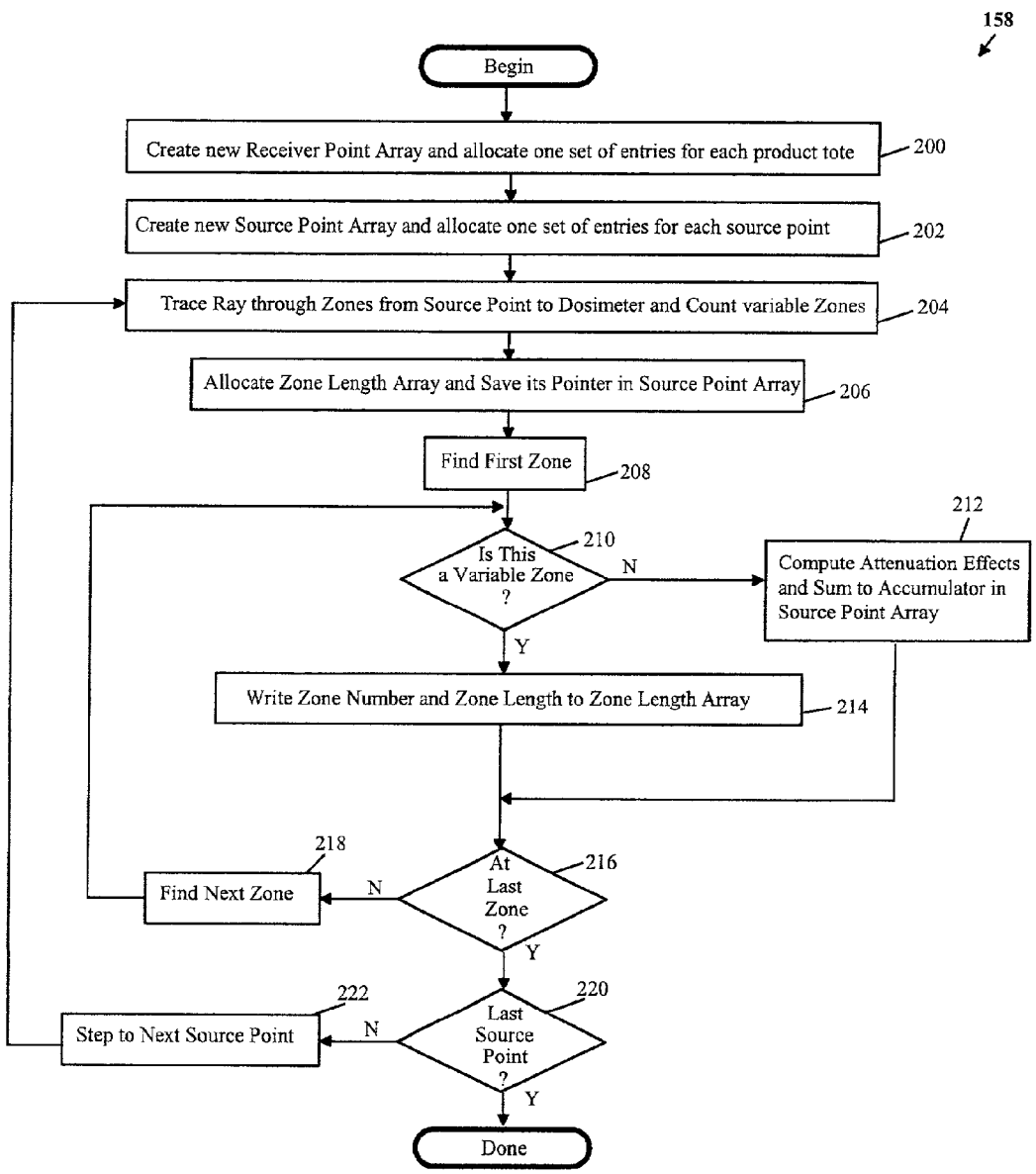
FIG. 6 illustrates a flowchart which is a more detailed description of the operation where the zone lengths are pre-calculated in accordance with one embodiment of the invention.

FIG. 6 illustrates flowchart 158 which is a more detailed description of operation 158 where the zone lengths are pre-calculated in accordance with one embodiment of the invention. This series of steps comprising flowchart 158 performs the extensive calculations associated with identifying and measuring the zone lengths traversed by each source point-dosimeter ray. In one embodiment the pre-calculated zone lengths are stored for future use as the method performs the multiple iterations through the loops of FIGS. 4–7. As described above, when the method determines in operation 156 of FIG. 4 that zone lengths corresponding to the current dosimeter have not yet been calculated, the method advances to operation 200 of FIG. 6. A dosimeter, once specified, will be used at every product tote location as the tote traverses the cell in one embodiment of the invention. Flowchart 158 initiates with operation 200 where a receiver point array is created and one set of entries in this array is allocated for each and every product tote position through the cell. It should be appreciated that a receiver refers to a dosimeter point at a particular position of the tote. Therefore, a dosimeter includes a number of receivers consisting of the dosimeter at the various stop locations through the cell i.e., the dosimeter is the sum of its receivers. In one embodiment, for every dosimeter a receiver point array is created. The receiver point array contains an entry for every position the dosimeter stops at through the cell where each entry represents one receiver.

The method of FIG. 6 then proceeds to operation 202 where a set of source point arrays is created, one for each entry in the receiver point array. The method then allocates a set of entries in each new source point array corresponding to the number of source points used to model the source. For example, a cell could contain 100 product tote positions i.e., stop locations, and 300 source points. The receiver point array, in operation 202, would contain 100 sets of entries, each of which would point to a separate source point array containing 300 entries per array. Thus, a total of 30,100 sets of entries would be allocated as a result of the processing thus far. It should be appreciated that the above example is provided for illustrative purposes only and not meant to be restrictive. The various data structures mentioned above are discussed in more detail in reference to FIG. 8.

Continuing with FIG. 6, the method next proceeds to operation 204 where a ray is traced from the current source point to the dosimeter. During the trace, the variable zones are tallied. As mentioned above, the variable zones contain product which may change from tote to tote. In one embodiment, the variable zones include shields placed on the outside of the totes. The method proceeds to operation 206 where the tally obtained in operation 204 is saved in the source point array and is used to allocate a zone length array. A pointer to this array is also saved in the source point array. In one embodiment, the zone length array includes an entry for a ray length in each variable zone and a zone length. The process moves to operation 208, where the first zone is detected. Next, in decision operation 210, the method determines whether the zone just entered is of the fixed or variable material type. If the zone is variable, the method advances to operation 214 where the zone number is written to the zone length array along with the length the current ray traces through the zone. The zone number is used in the dosage calculations of FIG. 5 to retrieve the composition of the product tote material occupying that zone. In one embodiment, the composition of the material in the variable zone is retrieved from the variable zone characteristics array as described in more detail with respect to FIG. 8.

Alternatively, if the process in decision operation 210 determines that the zone is of the fixed materials type, the method proceeds to step 212 where the attenuation effects of the zone length and the fixed zone material are summed to the accumulator in the source point array. In one embodiment, the fixed zone lengths and the fixed zone materials are constant, therefore, the effect on the dosage through the fixed zones is readily calculated. In another embodiment, the constant effects corresponding to the fixed zones are stored in the source point array as discussed in reference to FIG. 8. It should be appreciated that this pre-combination of fixed-materials effects simplifies the computational complexity during the simulation run. Upon completion of operation 212, the method moves to decision operation 216 where it is determined whether the last zone has been reached. If more zones remain, the method branches to operation 218 where the next zone is found. The method then proceeds back to step 210 where the zone is identified as fixed or variable as discussed above. The zone processing repeats as before until every zone along the current source point-dosimeter ray has been processed.

Returning to operation 216, if all zones along the source point-dosimeter ray have been processed, the method branches to decision operation 220 where the method determines whether the last source point has been processed. If the last source point has not been processed, the method branches to operation 222 where the next source point is selected. As mentioned above, each cobalt pencil is divided into numerous source points in one embodiment. Accordingly, each of the source points is processed through operation 204 where the ray tracing begins for the new source point-dosimeter ray. Every zone along this new ray is identified and cataloged as described above. Each source point-dosimeter ray is processed in turn, until no source points remain to be processed. Once all the source points for a particular receiver have been processed, decision operation 220 returns the method to operation 160 of FIG. 4 where the method proceeds with dose calculations as described below.

Figure 7:
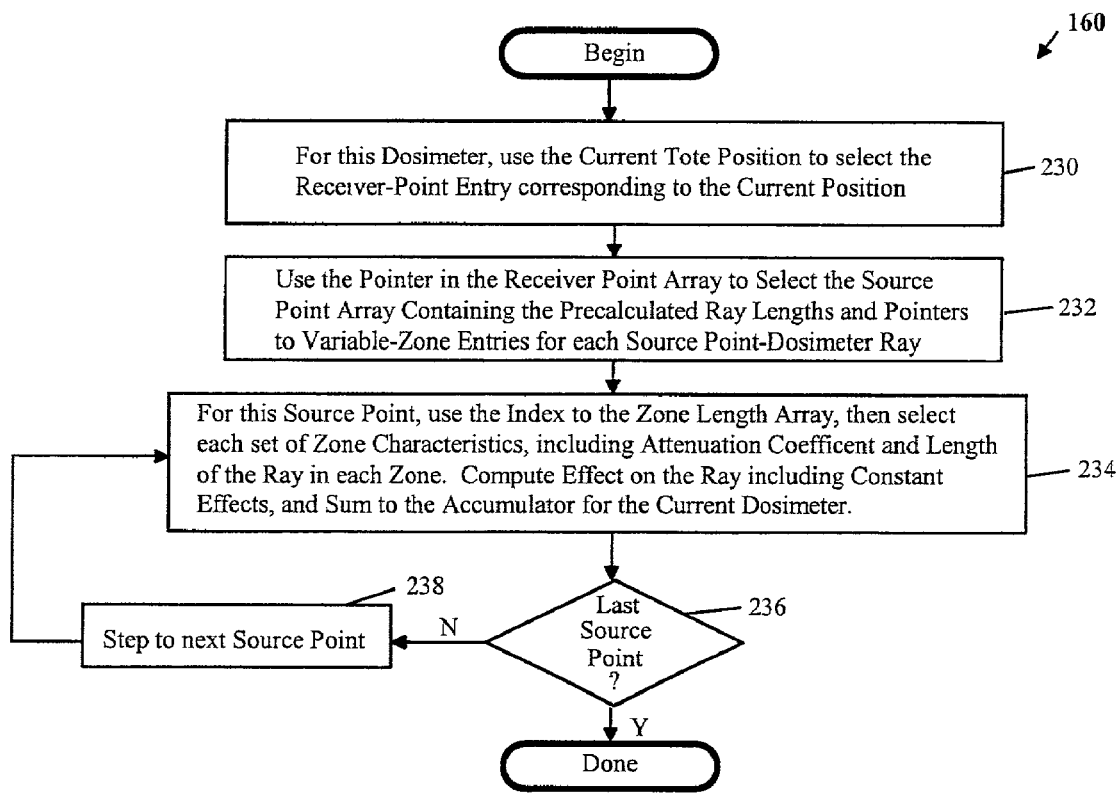
FIG. 7 illustrates a flowchart displaying a more detailed description of the operation where the accumulated dose arriving at the dosimeter from each of the source points, as affected by the fixed and variable zone materials between the source and dosimeter, is calculated in accordance with one embodiment of the invention.

FIG. 7 illustrates flowchart 160 displaying a more detailed description of operation 160 of FIG. 2 where the accumulated dose arriving at the dosimeter from each of the source points, as affected by the fixed and variable zone materials between the source and dosimeter, is calculated in accordance with one embodiment of the invention. One set of operations is performed for each source point-dosimeter ray, corresponding to the number of entries in the source point array, which was built as discussed in reference to FIG. 6. It should be appreciated that once the method has determined that it has zone length data available for the dosimeter under consideration in operation 156 of FIG. 4, it proceeds to operation 230 to begin calculating the dosage for the current dosimeter.

In operation 230 of FIG. 7, the method retrieves, from the dosimeter array, a pointer to the receiver point array corresponding to the current dosimeter. As will be discussed further with respect to FIG. 8, the dosimeter array contains the locations of the dosimeters within a product tote and the receiver point array includes the coordinates of each dosimeter within the cell at each stop location of the product tote through the cell. The method advances to operation 232 where a pointer to the source point array corresponding to the product tote at the current tote position is retrieved from the receiver point array. In one embodiment, the source point array includes the pre-calculated ray lengths described in reference to FIG. 6 and pointers to variable zone entries for each source point-dosimeter ray. Next, the method advances to operation 234 where the zone length and dose calculations are performed. In one embodiment, for each set of entries in the source point array where each entry corresponds to one source point-dosimeter ray, the method obtains a count of the number of variable zones and a pointer to the beginning of the zone length array for the corresponding source point. In another embodiment, for each set of entries in the zone length array, the length of the source point-dosimeter ray through each zone is obtained. In yet another embodiment, the method retrieves an index into the variable zone characteristics array, where it looks up the material type corresponding to the product tote in the current tote position.

As explained above, even though the material type in the variable zone array changes from cycle to cycle as the production schedule is read from the input, the zones and the length in each zone does not change. Using the variable zone material type and length just obtained, the method computes the attenuation of the source as it traverses this zone. Operation 234 then repeats the process for every zone in the current source point-dosimeter ray. Once the variable zone quantities have been accumulated, the method combines the partial result with the fixed zone effects to formulate a partial sum corresponding to the amount of dose received by this dosimeter during the current dwell time from this specific source point.

Continuing with FIG. 7, the method proceeds to decision operation 236 where it is determined whether the last source point-dosimeter pair has been processed. It should be appreciated that the same dosimeter is used for each source point here. If it is determined that there are more source points to be paired with the dosimeter, the next source point is selected in operation 238 and the operations described above are applied to the next source point-dosimeter pair. When all source points have been processed for the dosimeter, operation 236 branches to operation 162 of FIG. 4 where it moves on to the next dosimeter in the product tote.

The operations described with respect to FIGS. 4–7 are repeated for each dosimeter for each product tote as it proceeds through the irradiator cell. Of course, the distance between the stop locations can be made arbitrarily small in order to approximate continuous motion through the cell in one embodiment. It should be appreciated that some irradiation cells employ automated transport of the product through the cell via conveyors, tracks and the like while other cells utilize manual movement. In addition, the product may traverse the irradiation cell placed inside a container, i.e., product tote, or the product may proceed through the cell on a pallet. The flexibility of the method described above can accommodate any number of cell configurations as long as the geometric configuration and zones are capable of being established.

Figure 8:
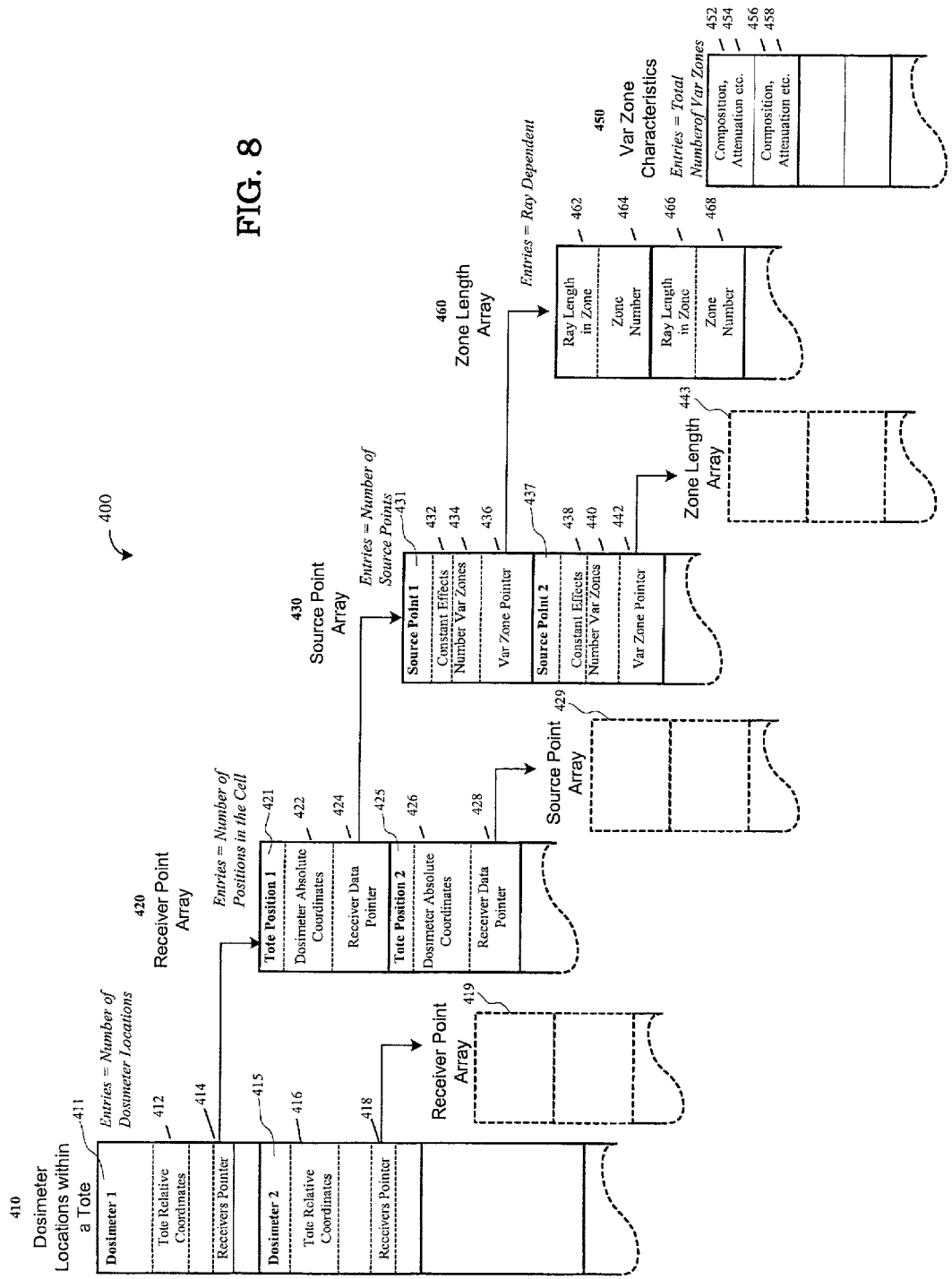
FIG. 8 illustrates a block diagram depicting the arrangement of the various data structures and their interrelationships in accordance with one embodiment of the invention.

FIG. 8 illustrates block diagram 400 depicting the arrangement of the various data structures and their interrelationships in accordance with one embodiment of the invention. Data structure 410 represents the dosimeter data array. The dosimeter data structure 410 contains the dosimeter locations within a product tote. In one embodiment, the number of entries in the dosimeter array 410 corresponds to the number of dosimeters within a tote. For example, if there are five dosimeters within a tote then there will be five entries in the dosimeter array. Dosimeter data structure 410 includes entries for dosimeter 1 411 and dosimeter 2 415. Within each entry are tote relative coordinates and a receivers pointer. As illustrated, tote relative coordinates 412 and receivers pointer 414 correspond to dosimeter 1 411, while tote relative coordinates 416 and receivers pointer 418 correspond to dosimeter 2. In one embodiment, the tote relative coordinates provide the location of the dosimeter within the product tote or product configuration. As mentioned above, a number of geometric conventions may be used to divide the product tote into grids to locate specific points within the tote. While FIG. 8 illustrates one dosimeter array, a dosimeter array is provided for each product tote being processed in the cell for which it is desired to simulate the dosage, in one embodiment. As discussed with respect to FIG. 4, the dosimeter array 410 is accessed in operation 164 for each dosimeter within a product tote.

Continuing with block diagram 400, receivers pointer 414 points to receiver point array 420. Receiver point array 420 includes an entry for each stop location of the product tote as it traverses the cell in one embodiment. For example, if as illustrated in FIGS. 1 and 2 the cell has 18 stop locations, then the receiver point array would contain 18 entries for each of the stop locations within the cell. Of course, the receiver point array in the described example correlates to a dosimeter within a tote such as dosimeter 1 411. As illustrated in receiver point array 420, there are entries for tote position 1 421 and tote position 2 425. Within the entry for tote position 1 421 are dosimeter absolute coordinates 422 and receiver data pointer 424. In one embodiment, dosimeter absolute coordinates contain the coordinates of the dosimeter within the cell as the product moves through the various stop locations i.e., receiver points for the dosimeter, of the cell. For example, tote position 1 421 may represent the enter position of the product tote, therefore, the dosimeter absolute coordinates 422 establish the location of dosimeter 1 411 within the cell while the tote is at tote position 1 421. Receiver data pointer 424 points to source point array 430. As illustrated, a source point array is created for each tote position contained within the receiver point array. As discussed above with respect to operation 200 of FIG. 6, a receiver point array is created for each dosimeter of each product tote.

Looking at source point array 430 of FIG. 8, source point entries are contained in the source point array 430. In one embodiment, a source point entry is included in the source point array 430 for each source point of the radiation source. For example, if there are 300 source points defined for the radiation source then 300 source point entries are included in the source point array 430. Within the entry for source point 1 431 are constant effects 432, the number of variable zones 434 and a variable zone pointer 436. As illustrated by FIG. 8, these entries are repeated for each source point. In one embodiment, constant effects 432 includes the cumulative effects of the fixed zones on the radiation dosage for the dosimeter-source point ray. As discussed above with respect to operation 212 of FIG. 6, the attenuation effects for the fixed zones associated with a source point-dosimeter ray are summed to an accumulator to provide the constant effects 432 in another embodiment. The number of variable zones 434 tallies the number of variable zones traversed by the source point-dosimeter ray traced from source point 1 431 to dosimeter 1 411. Of course, the number of variable zones are tallied for each of the source point entries for all the source point arrays. Similarly, the constant effects are stored for each of the ray traces. It should be appreciated that the source point arrays are created in operation 202 of FIG. 6, while the constant effects and the number of variable zones are calculated during operation 212 of FIG. 6 in one embodiment of the invention. Additionally, each source point entry of source point array 430 includes a variable zone pointer to zone length array 460.

Continuing with FIG. 8, there is a zone length array corresponding to each source point entry of the source point arrays as described in operation 206 of FIG. 6. Within zone length array 460 of FIG. 8, each entry includes the ray length 462 through each variable zone and the zone number 464 of the variable zone. Here, the ray length 462 is a portion of the source point-dosimeter ray from source point 1 431 to dosimeter 1 411 that passes through one variable zone. As discussed with respect to FIG. 6, the ray length in the zone and the zone number are written to the zone length array in operation 214. It should be appreciated that a ray length and a zone number is entered for each variable zone through which the corresponding source point-dosimeter ray traverses.

Variable zone characteristics array 450 of FIG. 8 includes an entry for each variable zone associated within the product totes. In one embodiment of the invention, product totes in the cell contain shields to further attenuate the dosage received by the product. These shields are treated as variable zones in one embodiment. The entries within the variable zone characteristics array 450 include the composition of the material in the variable zone and the attenuation coefficient of the material. For product totes composed of more than one zone, the variable zone characteristics array 450 would contain entries for each zone contained in the product tote. In one embodiment, an index for the variable zone number corresponds to the variable zone characteristics so that the effects on the radiation dosage through the variable and fixed zones for a source point-dosimeter ray can be calculated as described in operation 234 of FIG. 7. In a preferred embodiment, the variable zone characteristics are read from a production schedule defining the material composition and order of the products proceeding through the irradiator cell. The entries of the variable zone characteristics array 450 are stepped ahead as products proceed through the cell as described with respect to operation 182 of FIG. 5.

Figure 9:
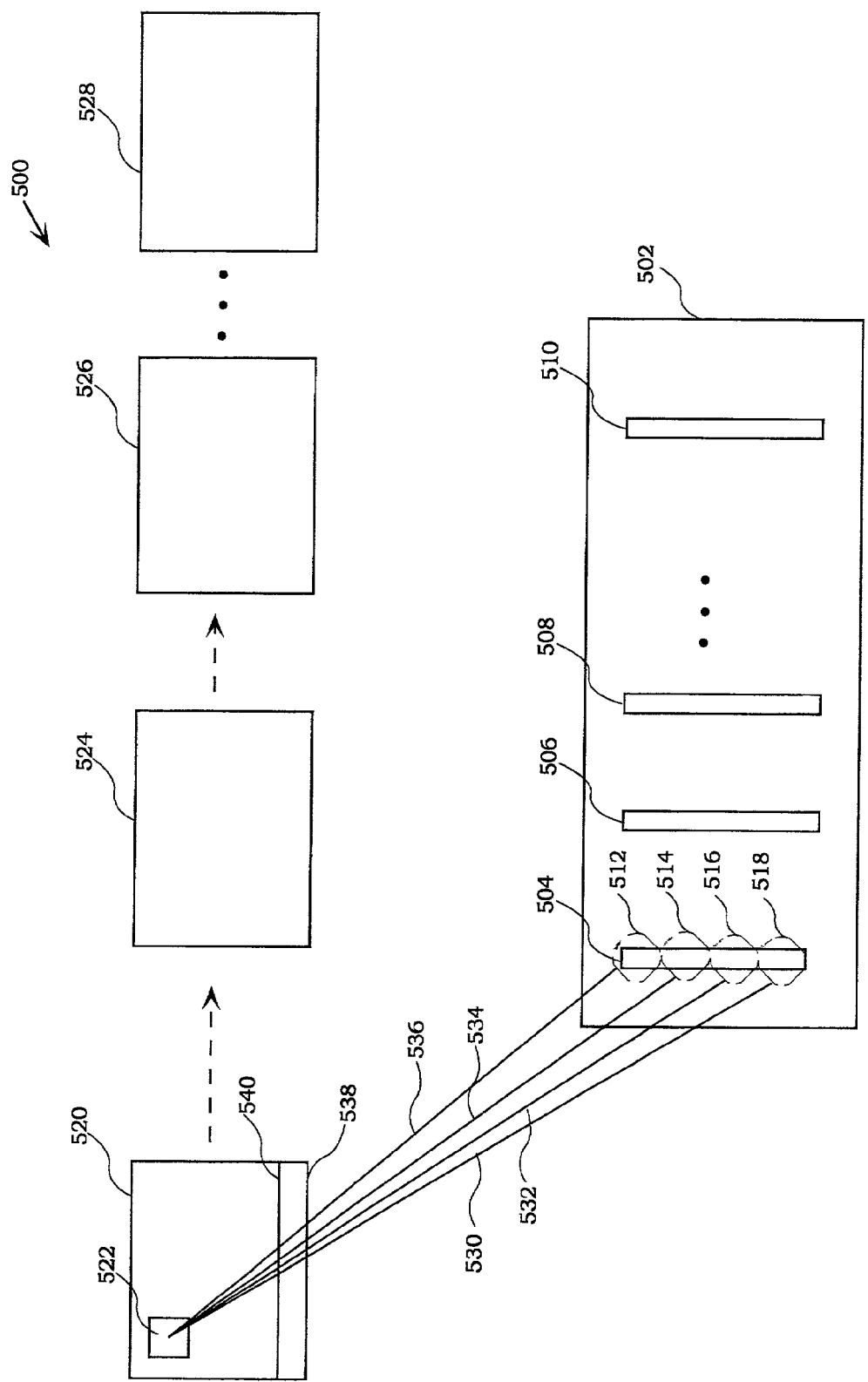
FIG. 9 illustrates a block diagram depicting a simulation of a product being irradiated in accordance with one embodiment of the invention.

FIG. 9 illustrates block diagram 500 depicting a simulation of product being irradiated in accordance with one embodiment of the invention. Block diagram 500 includes radiation source 502. Contained within radiation source 502 are pencil 1 504, pencil 2 506, pencil 3 508 and pencil n 510. In one embodiment, the pencils are cobalt pencils. Pencil 1 504 of the radiation source 502 is subdivided into four source points: source point 1 512, source point 2 514, source point 3 516 and source point 4 518. It should be appreciated that each pencil may be divided into any number of source points and that four source points was chosen for illustrative purposes only, therefore, it is not meant to be limiting. A source point-dosimeter ray is traced from each source point to each dosimeter in one embodiment. For example, source point-dosimeter ray 536 travels from source point 512 to dosimeter 522 located in product tote 520. As discussed with respect to operation 204 of FIG. 6, the variable zones traversed by the traced ray are counted here.

Continuing with FIG. 9, ray 536 can be divided further into zone lengths. For example, ray 536 consists of the following zone lengths: a) zone length 1 (L1) which consists of the distance from source point 512 to outer tote wall 538 of product tote 520; b) zone length 2 (L2) which consists of the distance from outer tote wall 538 to inner tote wall 540; and c) zone length 3 (L3) which consists of the distance from inner tote wall 540 to dosimeter 522. Zone lengths for the remainder of the source points (514, 516 and 518) are calculated similarly for the corresponding source point-dosimeter rays (534, 532 and 530). It should be appreciated that zone lengths for each source point-dosimeter ray for each source point of each pencil (pencil 2 506 through pencil n 510) is calculated for dosimeter 522. Similarly, the zone lengths for dosimeters located in product tote 2 524 through product tote n 528 are also calculated. In one embodiment, the length of the zones are pre-calculated and stored as discussed in reference to FIG. 6. Once the lengths are known the dosages are calculated as discussed with respect to FIG. 7.

While FIG. 9 illustrates three zone lengths for each source point-dosimeter ray, it should be appreciated that any number of zones may be encountered. For example, other product totes may be in the pathway of the traced ray in another embodiment. In addition, each product tote is capable of containing more than one dosimeter. Furthermore, the rays pass through multiple fixed and variable zones in another embodiment. As mentioned above, the product tote may contain a shield which is traversed by the source point-dosimeter ray. As product tote 520 is advanced to the next stop position within the cell, the method as described in FIGS. 3–7 is repeated for each stop position. Once the product tote 520 has completed the path through the cell, the calculated dosage for each dosimeter within the cell is presented. It should be appreciated that as the distance between the stop locations becomes infinitesimally small, the method approximates a continuous flow through the irradiator cell without stop locations.

It should be appreciated that in one embodiment, the invention may be represented as an apparatus. An irradiator cell, such as the irradiator cell of FIGS. 1 and 2, contains a radiation source. In a preferred embodiment the radiation source is Cobalt 60. However, other sources of radiation or treatment such as Gamma Rays, X-Radiation, Cesium, Neutrons, Light, Diffused Gas, Heat, Particles, Atoms, Atomic Particles and Sub-Atomic Particles may be utilized. In one embodiment, the cell is configured to contain the radiation from the radiation source. For example, the walls of the cell are made of concrete in one embodiment. In another embodiment, there may be no cell at all if, for example, the radiation source is composed of light. Additionally, the radiation source is contained in pencils arranged in a plane in another embodiment. It should be appreciated that the radiation source may be stored in a water bath at the bottom of the cell when not in use. A transport mechanism is used to move product through the cell past the radiation source. The transport mechanism is a conveyor belt stopping at defined locations for a period of time in one embodiment. In another embodiment, the transport mechanism moves continuously. As mentioned above the locations do not have to be equally spaced or the time periods do not have to be equal. In another embodiment the transport mechanism is a track on which a product tote rides and the product tote is manually moved between positions. In yet another embodiment, there is no transport mechanism. In still another embodiment, only a single product position exists.

For purposes of this application, a cell could be an enclosed area where the effects of the radiation source are constrained to affect only the product to be irradiated. A cell could also consist of an unenclosed area where the product undergoing treatment is exposed to the effects of a radiation or light source. Radiation sources and types typically include Cobalt, Gamma Rays, X-Radiation, Cesium, Neutrons, Light, Diffused Gas, Heat, Particles, Atoms, Atomic Particles and Sub-Atomic Particles.

The product to be irradiated is placed on the transport mechanism in a product tote in one embodiment. A computer simulates the passage of the product through the cell to determine the dosage level that will be received by the product according to the method described above. As mentioned in reference to FIGS. 3–9, the simulation identifies pre-calculated lengths between the dosimeter and the radiation source to determine the radiation dosage that a product will receive. It should be appreciated that the geometry of the cell is not limited to the embodiments of FIGS. 1 and 2. As mentioned above, the cell may be configured in any geometry as long as the ray lengths and zones described above are capable of being defined in the cell.

Furthermore, the apparatus may be a cell or compartment or a defined but not necessarily enclosed area containing a treating source, or an area where a product is exposed to the effects of a treating source. For example, the treating source may be light or a chemical or some combination of both where a treatment is supplied to the product through treatment rays where the lengths of the rays are capable of being pre-calculated based upon the geometry of the treatment compartment or treatment cell. In one embodiment, a general purpose computer may be included such as computer 121 of FIG. 2. Here, the general purpose computer 121 controls the robotics of the treatment cell, such as the transport mechanism, i.e., conveyor. In addition, the general purpose computer contains the code for executing the method described above with reference to FIGS. 3–7 for predicting a treatment dosage received by a product from the treatment source while the product is actually traversing the treatment cell. In one embodiment, the computer uses pre-calculated product positioning parameters to calculate the treatment dosage received by the product. Here, the pre-calculated product positioning parameters may include dosimeters and their location within the compartment, and zone lengths for treatment rays similar to the radiation rays and zone lengths described above with respect to FIGS. 3–7.

With the above embodiments in mind, it should be understood that the invention may employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations described herein that form part of the invention are useful machine operations. The invention also relates to a device or an apparatus for performing these operations. The apparatus may be specially constructed for the required purposes, or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

The invention can also be embodied as computer readable code on a computer readable medium. The computer readable medium is any data storage device that can store data which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. A computer simulation of radiation dosages received by a product to be passed along a radiation source in a cell, the product is to be stationary at a set number of locations in the cell, the simulation comprising:
   defining a point on the product;
   identifying pre-calculated lengths between the point on the product and the radiation source at each of the set of locations in the cell; and
   calculating a dosage of radiation to be received by the point on the product at each location, the calculating using the pre-calculated lengths.

2. The computer simulation as recited in claim 1, further comprising:
   accumulating the dosage of radiation received by the point at each location; and
   presenting the accumulated dosage.

3. The computer simulation as recited in claim 1, wherein the set number of locations in the cell is a single location.

4. The computer simulation as recited in claim 1, wherein the identifying pre-calculated lengths further includes:
   tracing rays between the radiation source and the point on the product; and
   identifying a set of zones traversed by the traced ray, each zone defining a segment of the ray.

5. The computer simulation as recited in claim 4, wherein the calculating a dosage of radiation includes:
   computing the effect on the ray as it passes through each of the set of zones.

6. The computer simulation as recited in claim 1, wherein the set number of locations within the cell are configured so as to simulate continuous movement by the product through the cell.

7. The computer simulation as recited in claim 1, the set of locations in the cell where the product is to be stationary defines receiver points, the receiver points providing a location of the point within the cell.

8. The computer simulation as recited in claim 4, wherein each segment of the ray is a zone length, the zone length being stored in a zone length array.

9. The computer simulation as recited in claim 1, wherein the pre-calculated lengths are stored in a data structure.

10. A computer implemented method for simulating a radiation dosage of a product traversing an irradiator cell, the irradiator cell having a radiation source from which rays of radiation emanate, comprising:
    identifying points on the product;
    identifying source points on the radiation source;
    defining zones within the irradiator cell, each zone being defined along a path;
    calculating effects of the zones on the rays of radiation travelling from the source points to the product along the paths; and
    accumulating the effects for each of the points on the product to provide a radiation dosage received by each of the points on the product.

11. The method as recited in claim 10, wherein the radiation source is cobalt.

12. The method as recited in claim 10, wherein the points on the product correspond to coordinates, the coordinates being configured to provide the location of the points within a product tote and to provide the location of the points within the irradiator cell.

13. The method as recited in claim 12, wherein the coordinates are stored in a data structure.

14. The method as recited in claim 10, wherein the zones include variable zones and fixed zones, the variable zones being configured to change from cycle to cycle, the fixed zones being configured to remain the same from cycle to cycle.

15. The method as recited in claim 14, wherein contents of the variable zones are stored in a variable zone characteristics array.

16. The method as recited in claim 15, wherein input for the variable zone characteristics array is provided by a production schedule.

17. A computer simulation method for predicting a radiation dosage received by dosimeters on a product, the product being exposed to radiation from a radiation source in an irradiator cell while stopping at a set of positions within the cell, comprising:
    defining a location for each of the dosimeters within the irradiator cell at each of the set of positions;
    calculating lengths from a set of source points on the radiation source to each of the dosimeters at each of the set of positions;
    storing the defined locations and the calculated lengths in a data structure; and
    determining the radiation dosage received by each of the dosimeters at each of the set of positions, the determining including,
    accessing the calculated lengths.

18. The method as recited in claim 17, further comprising:
    presenting the radiation dosage.

19. The method as recited in claim 17, wherein the calculating lengths from a set of source points further includes;
    tracing rays from each of the set of source points to each of the dosimeters at each of the set of positions;
    defining fixed zones and variable zones within the irradiator cell;
    determining effects of the fixed zones on the radiation dosage for each of the dosimeters at each of the set of locations; and
    storing the effects in the data structure.

20. The method as recited in claim 19, wherein the defining fixed zones further includes;
    tallying the number of variable zones that each of the traced rays for each of the set of source points; and
    storing the number of variable zones for each of the set of source points in the data structure.

21. The method as recited in claim 19, wherein the determining the radiation dosage received by each dosimeter further includes;
    obtaining a material composition for the variable zones; and
    summing effects of the fixed zones and partial dosages of the variable zones.

22. The method as recited in claim 19, wherein the defining fixed zones and variable zones within the irradiator cell further includes;
  accessing material compositions for each of the variable zones, the material compositions being stored in the data structure.

23. The method as recited in claim 21, wherein the material compositions are input from a production schedule.

24. The method as recited in claim 17, wherein the set of positions within the cell are configured so as to simulate continuous movement by the product through the cell.

25. A computer implemented method for simulating a radiation dosage to be received by a product in an irradiator compartment, comprising:
  reading a geometry of the irradiator compartment, the reading including,
    establishing zones,
    calculating constant zone lengths for each zone, and storing the constant zone lengths;
  defining a receiver point array, the receiver point array includes a set of entries for a dosimeter at a plurality of posit ions of the product as the product is advanced through the compartment;
  calculating a tracing of rays through each of the zones, the rays being defined between each of a plurality of source points to the dosimeter of the product as the product is advanced through the compartment, each ray being defined by ray segments, the ray segments having lengths defined by the constant zone lengths;
  calculating partial dosages for each of the traced rays;
  accumulating the partial dosages to provide a total dosage for the dosimeter once the product has completed its path through the compartment; and
  presenting the total dosage for the dosimeter of the product.

26. The method as recited in claim 25, further comprising:
  defining a plurality of additional receiver point arrays, each receiver point array includes a set of entries for a respective dosimeter at the plurality of positions of the product as the product is advanced through the compartment.

27. The method as recited in method 25, wherein the tracing rays through each of the zones further includes:
  advancing the stored constant zone lengths in conjunction with the product advancing through the compartment.

28. The method as recited in claim 25, wherein the product is contained in a product tote.

29. The method as recited in claim 25, wherein the zones are one of fixed zones and variable zones.

30. The method as recited in claim 28, wherein the product tote includes shields, the shields defining variable zones.

31. The method as recited in claim 25, wherein the product tote contains more than one zone.

32. The method as recited in claim 25, wherein the composition of a product is obtained from a production schedule.

33. A computer implemented method for simulating dosage levels for a product receiving radiation emanating from a treating source, comprising:
  establishing source points, the source points located on the treating source;
  calculating ray lengths for each of the source points, each of the ray lengths representing a path from the source points to a dosimeter associated with the product;
  identifying zone lengths for each of the ray lengths;
  identifying zone materials,
  computing an effect on the dosage level received by the dosimeter from the treating source by each zone material for each zone length; and
  accumulating a sum of partial dosages received by the dosimeter from each of the source points.

34. The method as recited in claim 33, wherein the zone materials include one of fixed zone materials and variable zone materials.

35. The method as recited in claim 34, wherein the zone lengths and an effect of the fixed zone materials on the zone lengths is stored in a data structure.

36. The method as recited in claim 35, wherein the computing an attenuation effect includes;
  accessing the zone lengths and the effect of the fixed zone material in the data structure.

37. The method as recited in claim 33, wherein the product is associated with multiple dosimeters.

38. The method as recited in claim 33, further comprising:
  presenting the sum.

39. A computer implemented method for predicting a dosage level received by a product as the product is processed through successive stop locations in an irradiator cell, the irradiator cell including a radiation source, the radiation source being defined by source points, the method comprising:
  reading the geometry of the irradiator cell, the geometry characterizing zones of the irradiator cell as fixed zones and variable zones;
  initializing a zone characteristics array and a dosimeter data array, the zone characteristics array including material compositions for the fixed zones and a default material composition for the variable zones, the dosimeter data array including coordinates for each dosimeter associated with the product;
  reading a production schedule, the production schedule containing names of each dosimeter for the product, a product dwell time for each stop location and variable material compositions for the variable zones, the variable material compositions being substituted for the default material composition;
  creating receiver point arrays, each receiver point array corresponding to each dosimeter of the dosimeter array, each receiver point array including an entry for each stop location of the product, each entry including dosimeter absolute coordinates;
  creating source point arrays, each source point array corresponding to each entry of each of the receiver point arrays, each source point array including fixed zone effects, the fixed zone effects reflecting a fixed zone attenuation;
  calculating a tracing of rays between each source point and each dosimeter;
  accessing a zone length array, the zone length array including a ray length for each ray through each zone;
  obtaining the variable material compositions for the variable zones;
  computing an attenuation of the radiation source for each of the variable zones of each ray length from each source point, the computing retrieving each ray length from the zone length array;
  accumulating the dosage level through each zone for each ray at each stop location for the dosimeter; and
  summing the accumulated dosage levels from each stop to provide a total dosage for each dosimeter through the irradiator cell.

40. The method as recited in claim 39, wherein the zone characteristics array, the dosimeter data array, the receiver point arrays and the source point arrays are stored in a data structure.

41. The method as recited in claim 40, wherein in conjunction with the product being processed through each stop location, data corresponding to the product in each of the arrays in the data structure is stepped ahead.

42. The method as recited in claim 39, further comprising:
presenting the total dosage for each dosimeter.

43. A computer implemented method for predicting an amount of radiation to be received by a product in a treatment compartment, comprising:
defining a material type for the product;
defining placements of the product within the treatment compartment;
pre-calculating lengths between a radiation source and the product for each of the placements within the treatment compartment; and
calculating a final predicted radiation dose, using the pre-calculated lengths, to be received by the product if subjected to treatment at each of the placements within the treatment compartment.

44. The method as recited in claim 43, wherein the lengths pass through one of a variable zone and a fixed zone.

45. The method as recited in claim 43, wherein the pre-calculated lengths are stored in a data structure.

46. The method as recited in claim 43, wherein the defining a material type for the product further includes:
reading a production schedule.

47. A computer implemented method for modeling a dosage level for a product to be exposed to a radiation source in an irradiator cell, comprising:
reading data files, the data files defining cell geometry, material compositions, and dosimetry specifications;
defining fixed zones and variable zones;
tracing rays, the rays being traced between source points of the radiation source and dosimeters of the product;
ascertaining zone lengths of the rays through each fixed and variable zone which the traced rays pass through;
identifying fixed zone materials and variable zone materials;
computing a fixed zone attenuation of the radiation source and a variable zone attenuation of the radiation source, the fixed zone attenuation and the variable zone attenuation being accumulated for each dosimeter location as the product advances through the irradiator cell; and
summing the accumulated fixed zone attenuation and variable zone attenuation to predict a dosage level for each dosimeter.

48. The method as recited in claim 47, further comprising:
presenting the predicted dosage level for each dosimeter.

49. The method as recited in claim 47, wherein the variable zone materials are provided by a variable zone characteristics array.

50. The method as recited in claim 47, wherein the ascertaining zone lengths further includes:
storing the zone lengths.

51. The method as recited in claim 50, wherein the computing a fixed zone attenuation of the radiation source and a variable zone attenuation of the radiation source further includes:
accessing the stored zone lengths.

52. A computer implemented method for determining dosages received by a product to be exposed to a treatment source at at least one defined location from the treatment source, the method comprising:
defining a point on the product;
defining fixed zones and variable zones;
identifying pre-calculated lengths between the point on the product and the treatment source at each of the at least one defined location; and
calculating a dosage of treatment to be received by the point on the product at each of the at least one defined location, the calculating using the pre-calculated lengths.

53. The method as recited in claim 52, wherein the treatment source is one of Gamma rays, X-radiation, neutrons, light, diffused gas, atoms, atomic particles and subatomic particles.

54. The method as recited in claim 52, wherein the treatment source and the product are contained within a treatment cell.

55. The method as recited in claim 52, further comprising:
calculating rays between the treatment source and the point on the product; and
determining the effects of the fixed zones and the variable zones on the calculated rays.

56. A computer readable medium having program instructions which when executed simulate radiation dosages received by a product to be passed along a radiation source in a cell, the product is to be stationary at a set number of locations in the cell, the computer readable media comprising:
program instructions for defining a point on the product;
program instructions for identifying pre-calculated lengths between the point on the product and the radiation source at each of the set of locations in the cell; and
program instructions for calculating a dosage of radiation to be received by the point on the product at each location, the calculating using the pre-calculated lengths.

57. The computer readable medium as recited in claim 56, further comprising:
program instructions for accumulating the dosage of radiation received by the point at each location; and
program instructions for presenting the accumulated dosage.

58. The computer readable medium as recited in claim 56, wherein the program instructions for identifying pre-calculated lengths further includes:
program instructions for tracing rays between the radiation source and the point on the product; and
program instructions for identifying a set of zones traversed by the traced ray, each zone defining a segment of the ray.

59. The computer readable medium as recited in claim 56, wherein the set number of locations within the cell are configured so as to simulate continuous movement by the product through the cell.

60. The computer readable medium as recited in claim 56, wherein the set number of locations within the cell is a single location.

61. An apparatus for irradiating a product, comprising:
a cell, the cell being configured to contain radiation;
a radiation source, the radiation source being located within the cell;
a transport mechanism;
a product, the product being transported using the transport mechanism through the cell, the product being associated with at least one dosimeter, the product and the dosimeter receiving a radiation dosage from the radiation source, the radiation dosage capable of being defined by a simulation prior to the product entering the cell, wherein the simulation identifies pre-calculated lengths between the dosimeter and the radiation source and uses the pre-calculated lengths to determine the radiation dosage received by the dosimeter.

62. The apparatus as recited in claim 61, wherein the transport mechanism is a conveyor, the conveyor being configured to advance the product through the cell.

63. The apparatus as recited in claim 61, wherein the radiation source is stored in water within the cell.

64. The apparatus as recited in claim 61, wherein the product is placed in a product tote.

65. The apparatus as recited in claim 64, wherein the product tote includes a shield, the shield being constructed to attenuate radiation from the radiation source.

66. The apparatus as recited in claim 61, wherein the radiation source is cobalt.

67. The apparatus as recited in claim 61, wherein the simulation is a computer simulation.

68. The apparatus as recited in claim 62, wherein the conveyor causes the product to dwell at a set of stop locations within the cell.

69. The apparatus as recited in claim 61, wherein the transport mechanism advances the product through the cell manually.

70. An apparatus for exposing a product to a treatment, comprising
   a treatment cell, the treatment cell being, configured to enclose a product path;
   a treatment source within the treatment cell;
   a product, the product being exposed to treatment from the treatment source while travelling along the product path; the exposure to the treatment of points on the product capable of being predicted by a computer simulation; the computer simulation being configured to obtain lengths of treatment rays from the treatment source to the points on the product based upon a geometry of the treatment cell, the lengths of the treatment rays being used to calculate a dosage of treatment received by the points on the product while travelling along the product path.

71. The apparatus as recited in claim 70, wherein the product is placed in a product tote.

72. The apparatus as recited in claim 70, wherein the treatment source is radiation.

73. The apparatus as recited in claim 70, wherein the treatment cell is an irradiator cell.

74. The apparatus as recited in claim 70, wherein the lengths of the treatment rays are stored in a data structure.

75. A treatment system, comprising;
   a general purpose computer for controlling robotics associated with a treatment compartment of the treatment system, the general purpose computer further including code for predicting treatment dosages to be received by a product from a treatment source located within the compartment, the code for predicting using pre-calculated product positioning parameters.

76. The treatment system as recited in claim 75, wherein the code identifies fixed zones and variable zones within the treatment compartment.

77. The treatment system as recited in claim 75, wherein the treatment dosages are radiation dosages.

78. The treatment system as recited in claim 75, wherein the product positioning parameters include dosimeters, zone lengths and source points.

79. The treatment system as recited in claim 75, wherein the product positioning parameters are stored in a data structure.

80. The treatment system as recited in claim 75, wherein the treatment source is one of Gamma rays, X-radiation, cesium, neutrons, light, diffused gas, heat, atoms, atomic particles and sub-atomic particles.

* * * * *